US010265485B2

(12) United States Patent
Shau et al.

(10) Patent No.: US 10,265,485 B2
(45) Date of Patent: Apr. 23, 2019

(54) MEDICATION CONCENTRATION DETECTING DEVICE FOR NEBULIZER

(71) Applicant: Industrial Technology Research Institute, Hsinchu (TW)

(72) Inventors: Yio-Wha Shau, Taipei (TW); Ma-Li Wang, Hsinchu (TW); Tzu-Wen Tsai, Taichung (TW); Tian-Yuan Chen, Hsinchu (TW); Hsin-Hsiang Lo, Hsinchu County (TW); Chun-Chuan Lin, Hsinchu (TW); Shih-Bin Luo, Hsinchu County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 728 days.

(21) Appl. No.: 14/968,219

(22) Filed: Dec. 14, 2015

(65) Prior Publication Data
US 2016/0346491 A1 Dec. 1, 2016

(30) Foreign Application Priority Data

May 27, 2015 (TW) .............................. 104208276 U

(51) Int. Cl.
*A61M 15/00* (2006.01)
*A61M 11/02* (2006.01)
(Continued)

(52) U.S. Cl.
CPC ........ *A61M 15/0065* (2013.01); *A61M 11/06* (2013.01); *A61M 16/0833* (2014.02);
(Continued)

(58) Field of Classification Search
CPC ...... A61M 11/00; A61M 11/02; A61M 11/06; A61M 15/0065; A61M 16/0816;
(Continued)

(56) References Cited

U.S. PATENT DOCUMENTS

| 33,924,252 | | 7/1968 | Duston |
|---|---|---|---|
| 5,277,175 | A | 1/1994 | Riggs et al. |

(Continued)

FOREIGN PATENT DOCUMENTS

| CN | 10270223 A | 5/2012 |
|---|---|---|
| CN | 203208473 U | 9/2013 |

(Continued)

OTHER PUBLICATIONS

Ron Leor et al., "A system for the measurement of drop volume of intravenous solutions, A system for the measurement of drop volume of intravenous solutions", Computers in Cardiology 1989, Proceedings., vol., No., Sep 19-22, 1989, pp. 405-406.
(Continued)

*Primary Examiner* — Jan Christopher L Merene
*Assistant Examiner* — Joseph D. Boecker
(74) *Attorney, Agent, or Firm* — Muncy, Geissler, Olds & Lowe, P.C.

(57) ABSTRACT

A medication concentration detecting device includes a medicine container, a three-way pipe, a light emitting member, a first light receiver and a processor. The medicine container has a chamber configured for accommodating nebulized medicine. The three-way pipe has a passageway connected to the chamber for the nebulized medicine to flow along the passageway. The light emitting member is disposed on the three-way pipe and configured for emitting a light beam toward the passageway. The first light receiver is disposed on the three-way pipe and configured for receiving the light beam and outputting a luminous flux signal. The processor is connected to the first light receiver and configured for calculating a luminous flux reference value according to the luminous flux signal. The luminous flux reference value is used for determining whether outputs a low nebulized medicine concentration warning.

19 Claims, 10 Drawing Sheets

(51) Int. Cl.
*A61M 11/06* (2006.01)
*A61M 16/08* (2006.01)
(52) U.S. Cl.
CPC . *A61M 2205/18* (2013.01); *A61M 2205/3306* (2013.01); *A61M 2209/02* (2013.01)
(58) Field of Classification Search
CPC .......... A61M 16/0833; A61M 2205/18; A61M 2205/3306; A61M 2205/3313; A61M 35/00; A61M 35/003; A61M 2209/02; G05D 11/138
See application file for complete search history.

(56) References Cited

U.S. PATENT DOCUMENTS

| | | | |
|---|---|---|---|
| 8,801,668 B2 | 8/2014 | Ali et al. | |
| 8,866,083 B2 | 10/2014 | Brigham et al. | |
| 2002/0033173 A1* | 3/2002 | Shofner, II | A61M 15/0065 128/200.22 |
| 2005/0066968 A1* | 3/2005 | Shofner | A61B 5/411 128/204.18 |
| 2005/0068528 A1* | 3/2005 | Altobelli | A61B 5/08 356/338 |
| 2008/0264412 A1* | 10/2008 | Meyer | A61M 15/0086 128/200.22 |
| 2009/0223513 A1* | 9/2009 | Papania | A61M 15/0065 128/200.16 |
| 2010/0326431 A1 | 12/2010 | Yu | |
| 2012/0090606 A1* | 4/2012 | Iwatschenko | A61M 11/02 128/203.15 |
| 2014/0166010 A1* | 6/2014 | Varga | A61M 16/14 128/203.29 |
| 2015/0020804 A1* | 1/2015 | Van Der Mark | A61M 11/00 128/203.14 |
| 2017/0065811 A1* | 3/2017 | Iwatschenko | A61M 11/06 |
| 2018/0126099 A1* | 5/2018 | Verjus | G01P 5/26 |
| 2018/0235475 A1* | 8/2018 | Svanberg | A61B 5/0075 |

FOREIGN PATENT DOCUMENTS

| | | | | |
|---|---|---|---|---|
| CN | 203829435 U | 9/2014 | | |
| CN | 203874239 U | 10/2014 | | |
| DE | 102010038163 A1 * | 4/2012 | ........... | A61K 9/0078 |
| EP | 0022438 A1 | 1/1981 | | |
| TW | 294599 B | 1/1997 | | |
| TW | M243201 U | 9/2004 | | |
| TW | 200916132 A | 4/2009 | | |

OTHER PUBLICATIONS

Norhayati Abu Bakar et al., "Detection of Fungicide in Water by ZnCdSe Quantum Dots Thin Film", Semiconductor Electronics (ICSE), 2010 IEEE International Conference on , vol., No., Jun. 28-30, 2010, pp. 283-285.

Kapila K Pahalawatta et al., "Particle Detection and Classification in Photoelectric Smoke Detectors Using Image Histogram Features", Digital Image Computing: Techniques and Applications (DICTA), 2013 International Conference on, vol., No., Nov. 26-28, 2013, pp. 1-8.

Alexander et al., "Integration of a multifunctional and multispectral optical sensor for automotive applications using surface mountable planar optical interconnect", Electronic System-Integration Technology Conference (ESTC), 2010 3rd , vol., No., Sep. 13-16, 2010, pp. 1-6.

Mario Pavlic et al., "Image based fog detection in vehicles", Intelligent Vehicles Symposium (IV), 2012 IEEE , vol., No., Jun. 3-7, 2012, pp. 1132-1137.

Amit Prabhakar et al., "C-shaped Embedded Polymer Waveguide for Evanescent Field Absorption based Lab on a Chip Biosensor", Systems in Medicine and Biology (ICSMB), 2010 International Conference on , vol., No., Dec. 16-18, 2010, pp. 67-70.

Prof. K.Y. Rajput et al, "Intelligent Street Lighting System Using Gsm", International Journal of Engineering Science Invention, vol. 2 Issue Mar. 31, 2013 , pp. 60-69.

Li, X.; Iervolino, E.; Santagata, F.; Wei, J.; Yuan, C.A.; Sarro, P.M.; Zhang, G.Q., "Miniaturized particulate matter sensor for portable air quality monitoring devices," in SENSORS, 2014 IEEE , vol., No., Nov. 2-5, 2014., pp. 1-4.

Chao-Ching Ho., "Nighttime Fire/Smoke Detection System Based on a Support Vector Machine", Mathematical Problems in Engineering vol. 2013 (2013), pp. 1-8.

Ron Knox., "Open-area Light Scattering Smoke Detection (OLSD)", pp. 1-11.

Gallen, R.; Cord et al., "Towards night fog detection through use of in-vehicle multipurpose cameras," in Intelligent Vehicles Symposium (IV), 2011 IEEE , vol., No., Jun. 5-9, 2011, pp. 399-404.

\* cited by examiner

FIG. 1

MEDICATION CONCENTRATION DETECTING DEVICE FOR NEBULIZER

CROSS-REFERENCE TO RELATED APPLICATIONS

This non-provisional application claims priority under 35 U.S.C. § 119(a) on Patent Application No(s). 104208276 filed in Taiwan, R.O.C. on May 27, 2015, the entire contents of which are hereby incorporated by reference.

TECHNICAL FIELD

The disclosure relates to a medication concentration detecting device for a nebulizer.

BACKGROUND

In recent years, respiratory diseases such as cystic fibrosis and Asthma are among the worldwide leading causes of death. A nebulizer is a type of drug deliver commonly used for the treatment of such diseases. The nebulizer is used to administer medication in the form of a mist for being inhaled into the lungs. In details, the nebulizer uses oxygen, compressed air or ultrasonic power to break up medical solutions and suspensions into small aerosol droplets that can be directly inhaled from the mouthpiece of the nebulizer.

SUMMARY

One embodiment of the disclosure provides a medication concentration detecting device for nebulizer. The medication concentration detecting device includes a medicine container, a three-way pipe, a light emitting component, a first light receiver and a processor. The medicine container has a chamber configured for accommodating nebulized medicine. The three-way pipe has a passageway connected to the chamber for the nebulized medicine to flow along the passageway. The light emitting component is disposed on the three-way pipe and configured for emitting a light beam toward the passageway. The first light receiver is disposed on the three-way pipe and configured for receiving the light beam and outputting a luminous flux signal. The processor is connected to the first light receiver and configured for calculating a luminous flux reference value according to the luminous flux signal. The luminous flux reference value is used for determining whether outputs a low nebulized medicine concentration warning.

BRIEF DESCRIPTION OF THE DRAWINGS

The present invention will become better understood from the detailed description given hereinbelow and the accompanying drawings which are given by way of illustration only and thus are not limitative of the present invention and wherein:

FIG. 1 is a perspective view of a medication concentration detecting device according to a first embodiment of the disclosure being connected to a tube;

DETAILED DESCRIPTION

Figure 2:
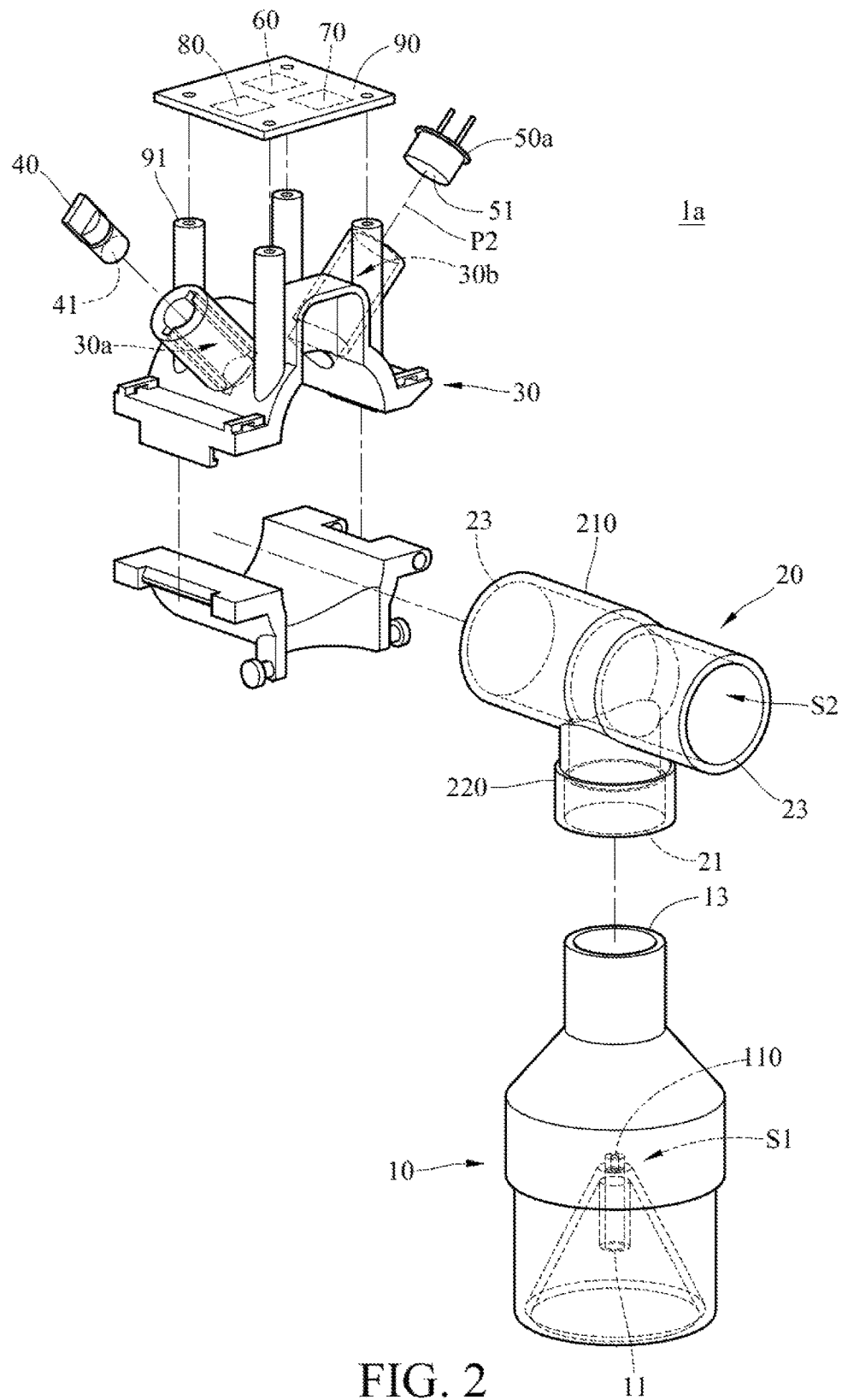
FIG. 2 is an exploded view of the medication concentration detecting device according to the first embodiment of the disclosure.

In the following detailed description, for purposes of explanation, numerous specific details are set forth in order to provide a thorough under Standing of the disclosed embodiments. It will be apparent, however, that one or more embodiments may be practiced without these specific details. In other instances, well-known structures and devices are schematically shown in order to simplify the drawing.

Figure 1:
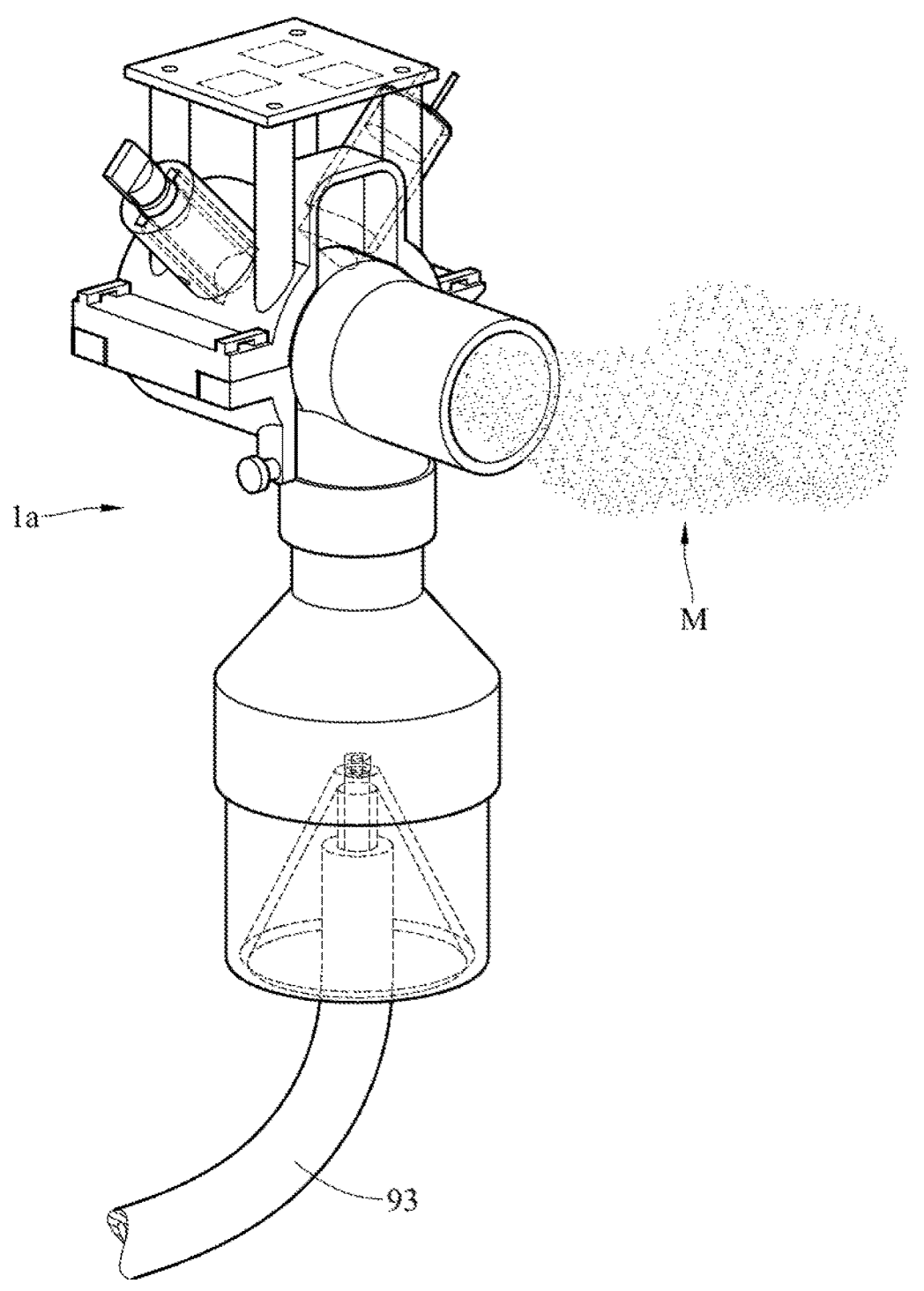

Please refer to FIG. 1, which is a perspective view of a medication concentration detecting device according to a first embodiment of the disclosure being connected to a tube.

This embodiment provides a medication concentration detecting device 1a for nebulizer. As shown in FIG. 1, the medication concentration detecting device 1a is connected to a tube 93, and the tube 93 is connected to an oxygen provider (not shown) for providing pure oxygen to the medication concentration detecting device 1a. Therefore, the medicine M in the medication concentration detecting device 1a will be nebulized for patient to inhale. In addition, by using the medication concentration detecting device 1a, patient is capable of detecting whether a concentration of the nebulized medicine M is insufficient.

Figure 3A:
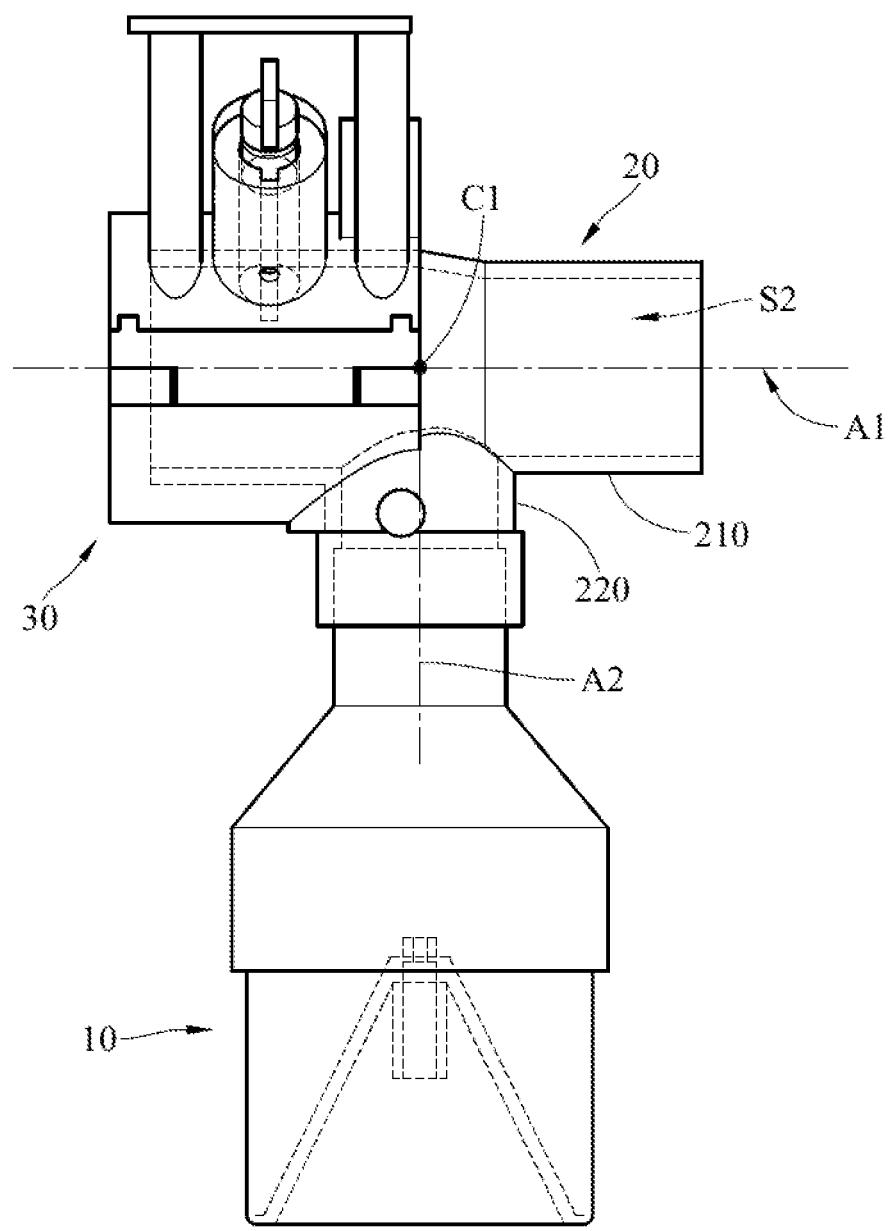
FIG. 3A is a side view of the medication concentration detecting device according to the first embodiment of the disclosure.
Figure 3B:
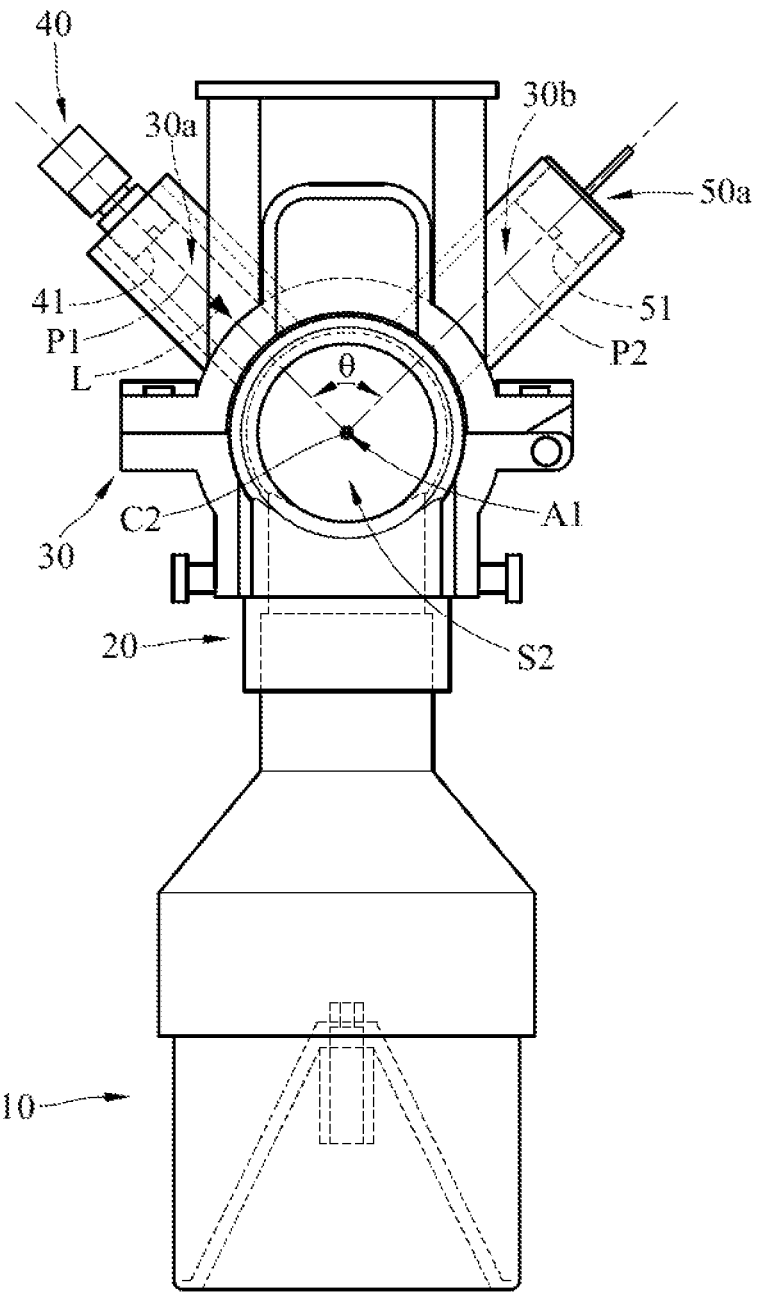
FIG. 3B is a front view of the medication concentration detecting device according to the first embodiment of the disclosure.
Figure 4:
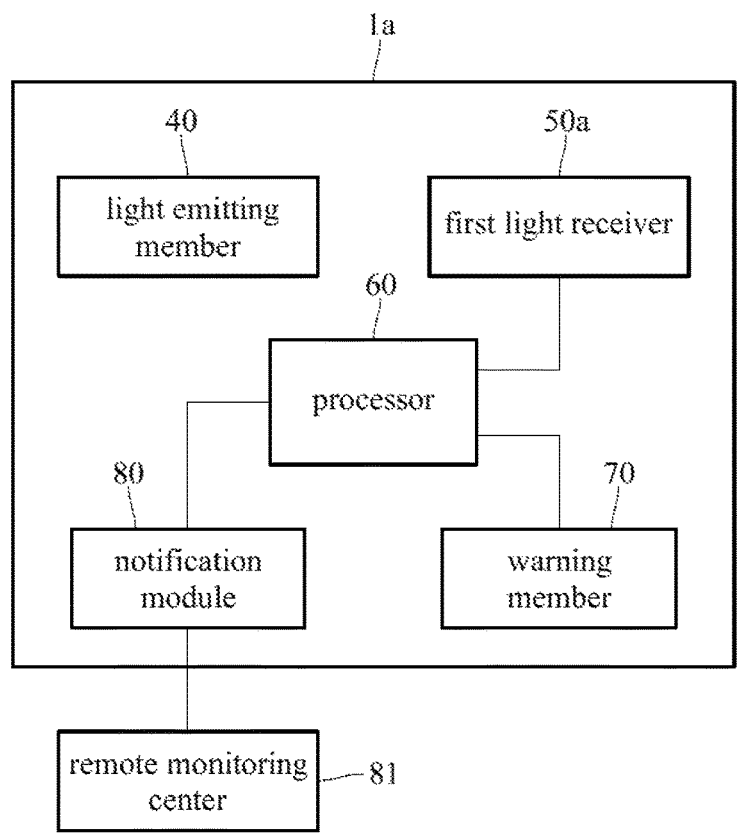
FIG. 4 is an electrical connection diagram of the medication concentration detecting device according to the first embodiment of the disclosure.
Figure 5:
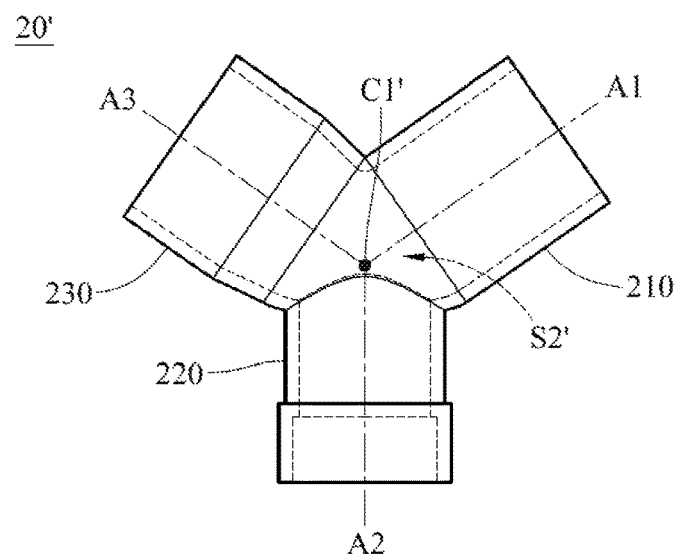
FIG. 5 is a perspective view of a three-way pipe according to a second embodiment of the disclosure.
Figure 6:
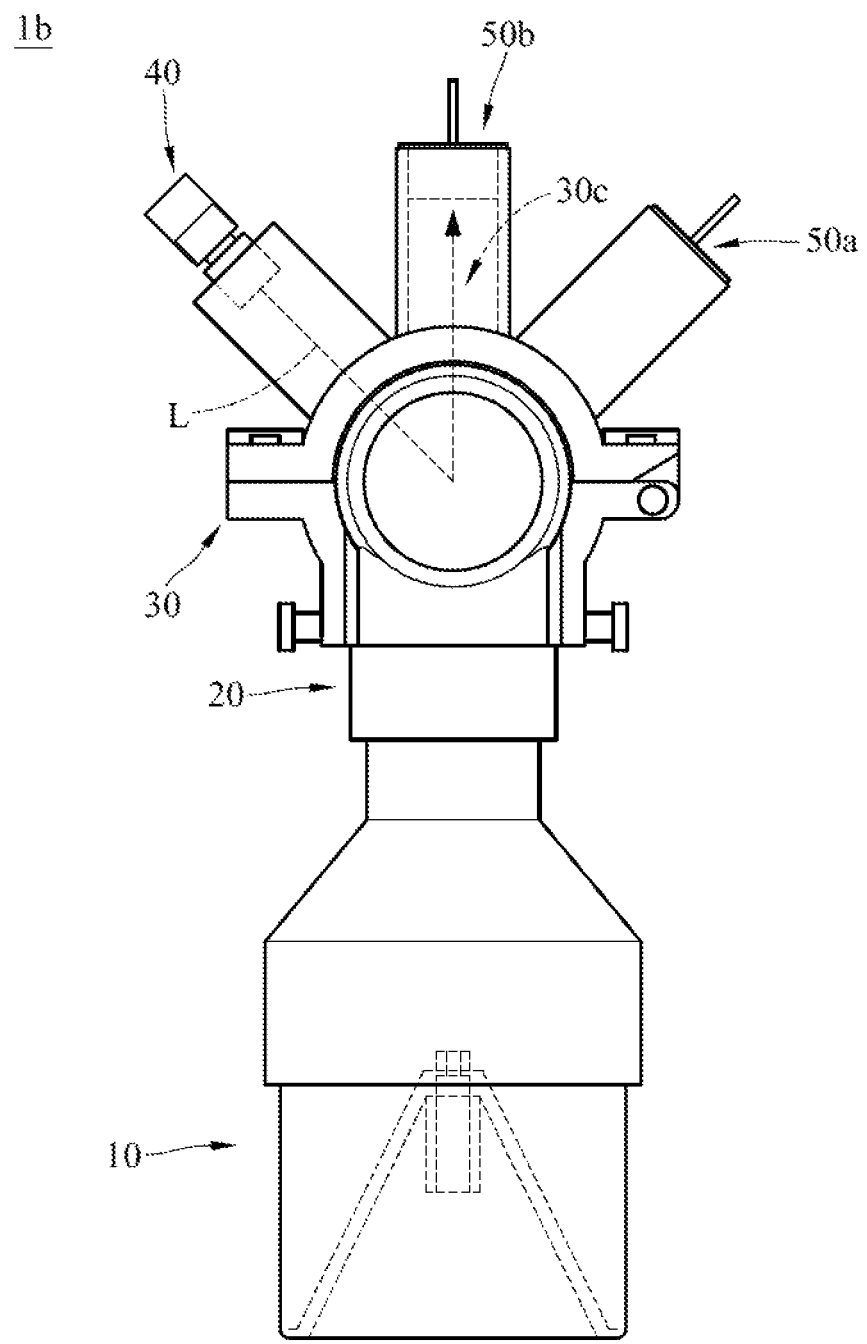
FIG. 6 is a front view of a medication concentration detecting device according to a third embodiment of the disclosure.
Figure 7:
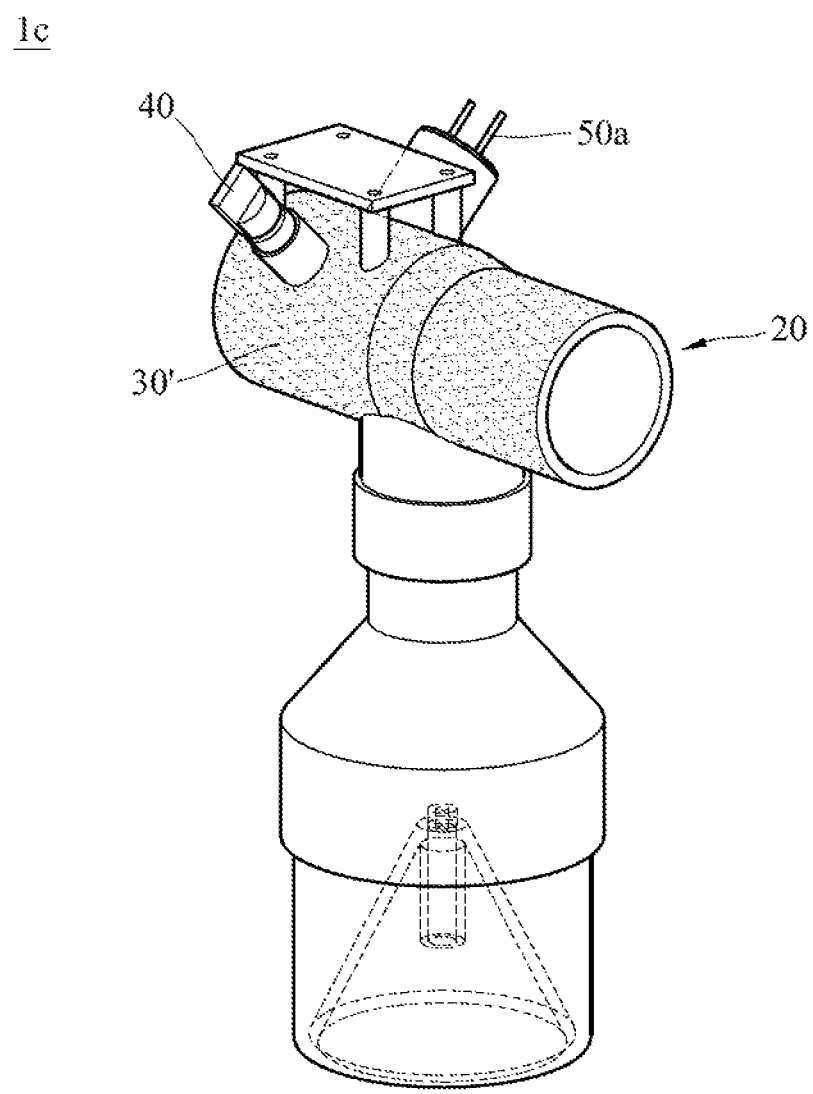
FIG. 7 is a perspective view of a medication concentration detecting device according to a fourth embodiment of the disclosure.
Figure 8A:
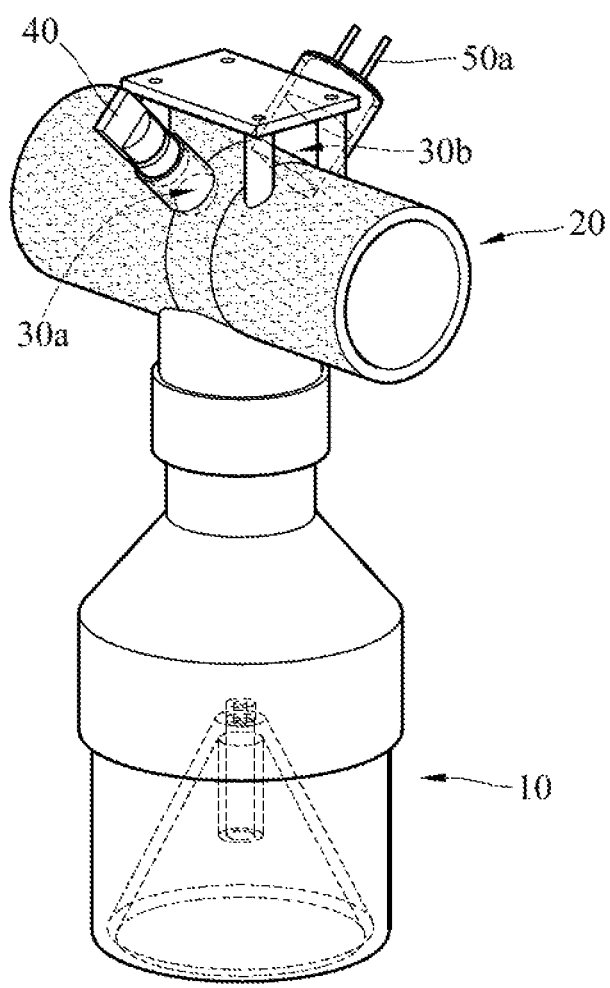
FIG. 8A is a perspective view of a medication concentration detecting device according to a fifth embodiment of the disclosure.
Figure 8B:
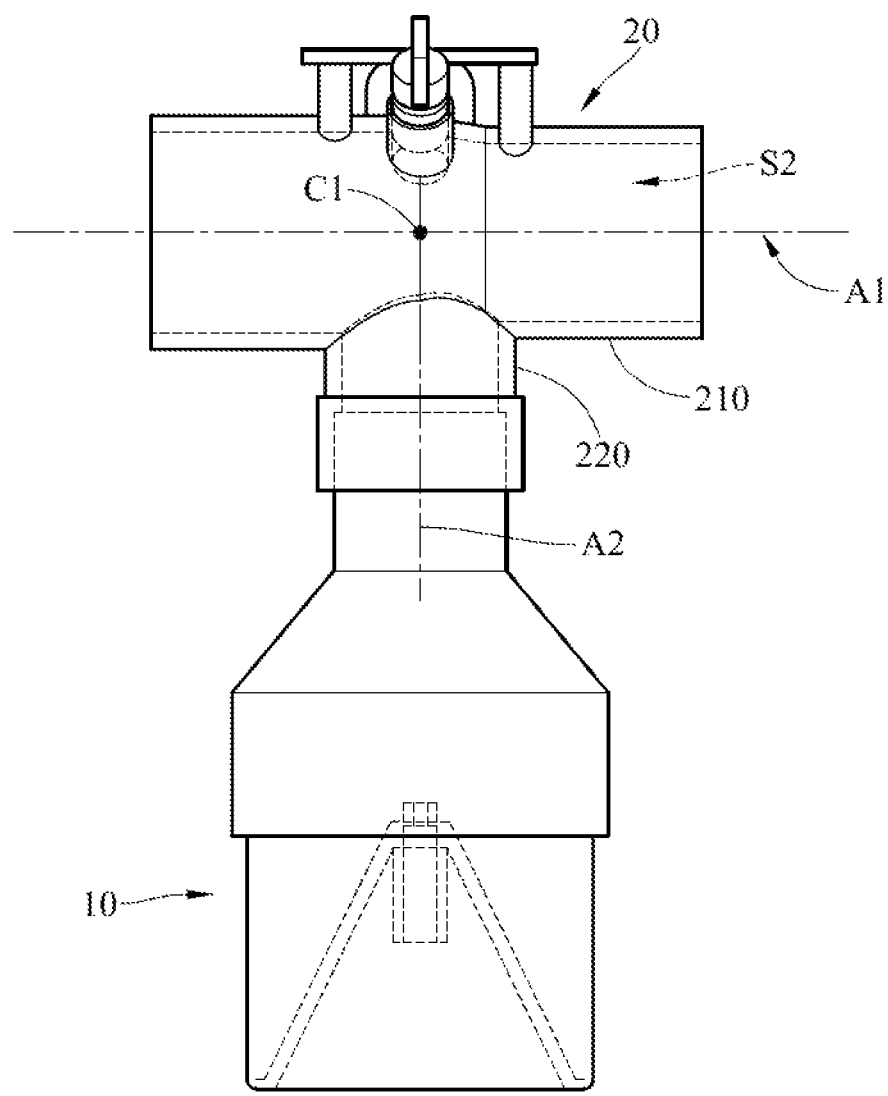
FIG. 8B is a side view of the medication concentration detecting device according to the fifth embodiment of the disclosure.
Figure 8C:
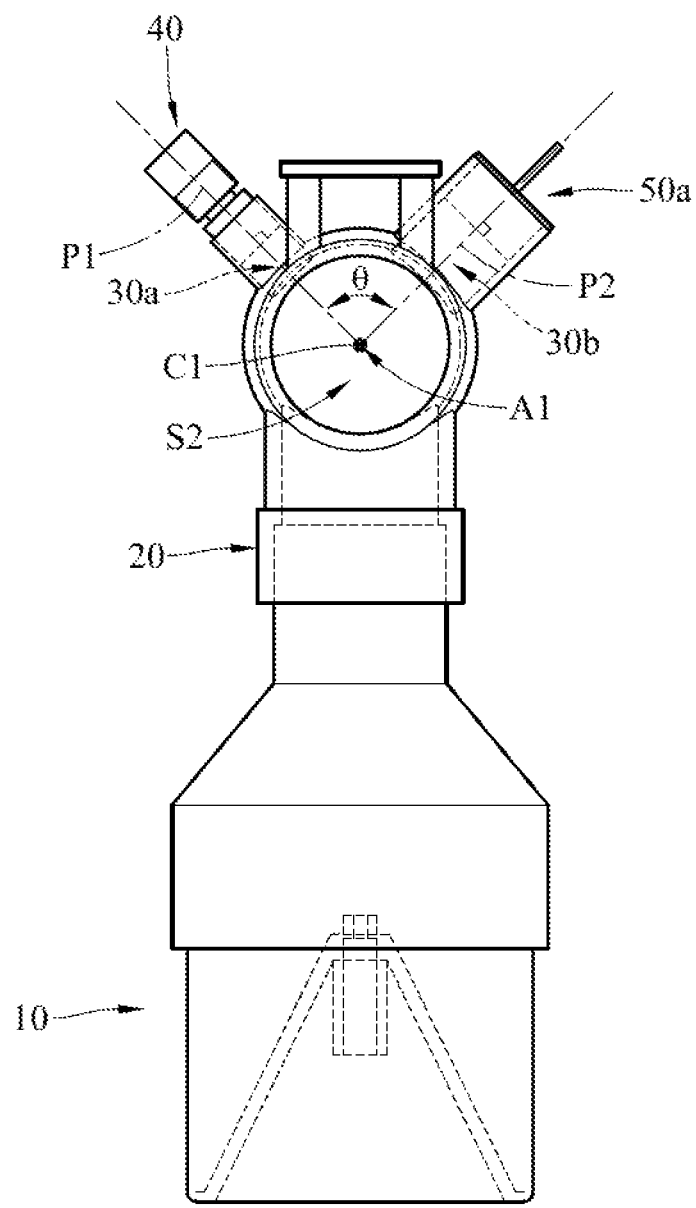
FIG. 8C is a front view of the medication concentration detecting device according to the fifth embodiment of the disclosure.

In details, please refer to FIG. 2 to FIG. 4. FIG. 2 is an exploded view of the medication concentration detecting device according to the first embodiment of the disclosure. FIG. 3A is a side view of the medication concentration detecting device according to the first embodiment of the disclosure. FIG. 3B is a front view of the medication concentration detecting device according to the first embodiment of the disclosure. FIG. 4 is an electrical connection diagram of the medication concentration detecting device according to the first embodiment of the disclosure.

As shown in FIG. 2, the medication concentration detecting device 1a includes a medicine container 10, a three-way pipe 20, a light-blocking component 30, a light emitting component 40, a first light receiver 50a and a processor 60. In addition, the medication concentration detecting device 1a is equipped with a warning component 70 and a notification module 80.

The medicine container 10 has a first air inlet 11, a first air outlet 13 and a chamber S1. The so called chamber S1 is configured for accommodating the nebulized medicine M. The first air inlet 11 and the first air outlet 13 are connected to the chamber S1 so that the nebulized medicine M may flow out of the chamber S1 through the first air outlet 13. The tube 93 is connected to the first air inlet 11, and thus the pure oxygen in the tube 93 may flow into the chamber S1 through the first air inlet 11. An atomizer 110 is disposed in the chamber S1, which causes the pure oxygen to flow through a liquid medicine at a high velocity so as to turn it into an aerosol (e.g. the nebulized medicine M) by the pressure difference.

Then, please see both FIG. 2 and FIG. 3A. In this embodiment, the three-way pipe 20 is a T-shaped three-way pipe detachably disposed on the medicine container 10. In details, the three-way pipe 20 includes a first pipe 210 and a second pipe 220. The first pipe 210 and the second pipe 220 connected to each other surround and define a T-shaped passageway S2. A first central axis A1 of the first pipe 210 and a second central axis A2 of the second pipe 220 intersect at a point C1. In addition, the three-way pipe 20 has a second air inlet 21 and two second air outlets 23, the second air inlet 21 and the two second air outlet 23 are connected to the passageway S2. The second air inlet 21 is located at one end of the second pipe 220. The two second air outlets 23 are located at two ends of the first pipe 210 which are opposite to each other, respectively. The second air inlet 21 is connected to the first air outlet 13 of the medicine container 10, allowing the nebulized medicine M to flow into the passageway S2 from the chamber S1. Furthermore, the second air outlet 23 is connected to a mouthpiece (not shown) configured for the patient to inhale the nebulized medicine M.

In this embodiment, the light-blocking component 30 is detachably disposed on the three-way pipe 20 for covering the surface of the three-way pipe 20, thereby preventing ambient light from transmitting through the passageway S2 to disturb a detection of a concentration of the nebulized medicine M. In this embodiment, the light-blocking component 30 is made of, for example, paper, metal or plastic.

In addition, the light-blocking component 30 has a first light transmitting area 30a and a second light transmitting area 30b. The light emitting component 40 and the first light receiver 50a can communicate to each other through the first light transmitting area 30a and the second light transmitting area 30b for conveniently detecting the concentration of the nebulized medicine M in the three-way pipe 20.

The light emitting component 40 disposed on the light-blocking component 30 and corresponding to the first light transmitting area 30a is not directly disposed on the three-way pipe 20 as shown in FIG. 3B, but the present disclosure is not limited thereto. In other embodiments, the light emitting component 40 is directly disposed on the three-way pipe 20. The light emitting component 40 is, for example, a laser diode configured to emit a light beam L toward the passageway S2. The light beam L has a wavelength in the range from 350 nm to 1200 nm. However, the present disclosure is not limited by the type of the light emitting component 40. In other embodiments, the light emitting component 40 is a light emitting diode (LED).

The first light receiver 50*a* disposed on the light-blocking component 30 and corresponding to the second light transmitting area 30*b* is not directly disposed on the three-way pipe 20 as shown in FIG. 3B, but the present disclosure is not limited thereto. In other embodiments, the first light receiver 50*a* is directly disposed on the three-way pipe 20. The first light receiver 50*a* is, for example, a light sensor having photosensitive elements. The photosensitive elements convert an optical signal into an electrical signal. The so called photosensitive element includes, for example, at least one of a photoresistor (also called light-dependent resistor or photoconductor), a charge coupled device (CCD), a complementary metal-oxide semiconductor (CMOS), photodiode, ambient light sensor, a valance photodiode or photomultiplier (PMT).

Please refer to both FIG. 2 and FIG. 3B, the light emitting component 40 has a light emitting surface 41 corresponding to the first light transmitting area 30*a*, and the light emitting surface 41 has a first central line P1 which is perpendicular to the light emitting surface 41. The first light receiver 50*a* has a light receiving surface 51 corresponding to the second light transmitting area 30*b*, and the light receiving surface 51 has a second central line P2 which is perpendicular to the light receiving surface 51. Both of the first central line P1 and the second central line P2 penetrate through the first pipe 210 of the three-way pipe 20 and intersect with the first central axis A1 of the first pipe 210 at a point C2, and the first central line P1 and the second central line P2 form an angle 9 at the point C2.

The processor 60 is disposed on the three-way pipe 20 and configured for calculating or transmitting signals. In this embodiment, the processor 60 is electrically connected to the first light receiver 50*a* through a wired connection, but the present disclosure is not limited thereto. In other embodiments, the processor 60 is electrically connected to the first light receiver 50*a* through a wireless connection.

The warning component 70 is disposed on the three-way pipe 20 and electrically connected to the processor 60. In this embodiment, the warning component 70 is, for example, a buzzer, a horn, a warning light or a vibrating motor.

The notification module 80 is disposes on the three-way pipe 20 and electrically connected to the processor 60, In addition, the notification module 80 is configured for connecting to a remote monitoring center 81.

Specifically, as shown in FIG. 2, in this embodiment, the processor 60, the warning component 70 and the notification module 80 are disposed on a frame object 90 which is supported by a plurality of legs 91 assembled on the light-blocking component 30. In this embodiment, the frame object 90 is, for example, a circuit board. The processor 60, the warning component 70 and the notification module 80 are assembled with the light-blocking component 30 as an integral assembly, which is convenient for the user to operate, but the present disclosure is not limited thereto. In other embodiments, the processor 60, the warning component 70 and the notification module 80 can be assembled into a box-like container (not shown), and the rest components of the medication concentration detecting device 1*a* are connected to the container through a wired connection.

Then, please refer to both FIG. 3B and FIG. 4. When the light beam L is emitted into the passageway S2 from the first light transmitting area 30*a* along an extending direction of the first central line P1, the light beam L hitting the nebulized medicine M is scattered. Part of the scattered light beam L leaves the passageway S2 through the second light transmitting area 30*b* of the light-blocking component 30 and then reaches the light receiving surface 51 of the first light receiver 50*a*. When the first light receiver 50*a* receives the scattered light beam L, it transmits a luminous flux signal to the processor 60. The processor 60 calculates a luminous flux reference value according to the luminous flux signal transmitted from the first light receiver 50*a*. The luminous flux reference value is used for determining whether outputs a low nebulized medicine concentration warning. The low nebulized medicine concentration warning is used for notifying the patient that the concentration of the nebulized medicine M is insufficient.

Specifically, when the luminous flux reference value calculated by the processor 60 is lower than a predetermined lower limit value, which indicates the concentration of the nebulized medicine M is insufficient, the processor 60 outputs a warning signal to the warning component 70. The warning component 70 generates warning information according to the warning signal. The warning information is not limited to visual information or audio information. The processor 60 also outputs a notification signal to the remote monitoring center 81 for noticing health care workers.

Moreover, since light intensity of the scattered light beam L decreases with increase of distance, the first light receiver 50*a* and the light emitting component 40 are preferred to be arranged in a manner that the second central line P2 of the first light receiver 50*a* and the first central line P1 of the light emitting component 40 form an angle θ less than 180 degrees. In this embodiment, the angle θ is further defined in a range from 80 degrees to 100 degrees for ensuring most of the scattered light beam L received by the first light receiver 50*a* came from a region of the highest concentration of the nebulized medicine M in the passageway S2 of the three-way pipe 20. Specifically, the region is where the point C2 is located, and thereby the detection accuracy of the concentration of the nebulized medicine M is improved.

Besides, in other embodiments, the notification module 80 can be omitted from the medication concentration detecting device. In such a case, the medication concentration detecting device warns patient that the nebulized medicine M is insufficient by the warning component 70.

Then, please refer to FIG. 5, which is a perspective view of a three-way pipe according to a second embodiment of the disclosure. In the second embodiment, only differences between the second embodiment and the first embodiment will be explained because the second embodiment is similar to the first embodiment.

In this embodiment, the three-way pipe is a Y-shaped three-way pipe 20'. As shown in FIG. 5, the three-way pipe 20' includes a first pipe 210, a second pipe 220 and a third pipe 230. The first pipe 210, the second pipe 220 and the third pipe 230 connected to one another surround and define a Y-shaped passageway S2'. In addition, a first central axis A1 of the first pipe 210, a second central axis A2 of the second pipe 220 and a third central axis A3 of the third pipe 230 intersect at a point C1'.

Please refer to FIG. 6, which is a front view of a medication concentration detecting device according to a third embodiment of the disclosure. In the third embodiment, only differences between the third embodiment and the first embodiment will be explained because the third embodiment is similar to the first embodiment. In addition, for purposes of clear explanation, the processor 60, the warning component 70, the notification module 80, the frame object 90 and the legs 91 are omitted in FIG. 6.

In the third embodiment that the light emitting component 40 is a laser diode, the intensity of the light beam L emitted by the laser diode 40 is decayed over duration of use, thereby decreasing the intensity of the light beam L (i.e. the amount of light) received by the first light receiver 50*a*, which results in an inaccurate detection of the concentration of the nebulized medicine M.

Accordingly, the medication concentration detecting device 1*b* further includes a second light receiver 50*b* disposed between the light emitting component 40 and the first light receiver 50*a*. In addition, the light-blocking component 30 has a third light transmitting area 30*c* corresponding to the second light receiver 50*b*.

When the intensity of the light beam L is decreased with the increase of the use duration of the laser diode 40, the second light receiver 50*b* is still able to receive enough amount of light for detecting the concentration of the nebulized medicine M because the second light receiver 50*b* is closer to the light emitting component 40 than the first light receiver 50*a*.

Please refer to FIG. 7, which is a perspective view of a medication concentration detecting device according to a fourth embodiment of the disclosure. In this embodiment, only differences between the fourth embodiment and the first embodiment will be explained because the fourth embodiment is similar to the first embodiment.

The designs that allow the light-blocking component to block ambient light from entering the passageway in the three-way pipe 20 fall within the scope of the present disclosure. For example, the fourth embodiment provides a medication concentration detecting device 1*c* having a light-blocking component 30', the light-blocking component 30' is a layer coated on the surface of the three-way pipe 20 by a coating process. In this or other embodiments, the light-blocking component 30' may be a layer of pigment. In addition, in other embodiments, the light-blocking component 30' and the three-way pipe 20 may be integrated into a single unit. In such a case, the light-blocking component 30' may be a matte surface on the three-way pipe 20 which is not pervious to light.

As shown in FIG. 7, the most surface of the three-way pipe 20 is covered with the light-blocking component 30', thereby reducing the influence of the ambient light on the optical detection in the passageway S2 of the three-way pipe 20.

In addition, the present disclosure is not limited to the connection between the light emitting component 40, the first light receiver 50*a* and the three-way pipe 20. As shown in FIG. 7, in this embodiment, the light emitting component 40 and the first light receiver 50*a* are respectively disposed on two additional pipes mounted on the three-way pipe 20. In other embodiments, the light emitting component 40 and the first light receiver 50*a* are directly attached to the light transmitting areas formed on the light-blocking component 30'.

Then, please refer to FIG. 8A to FIG. 8C. FIG. 8A is a perspective view of a medication concentration detecting device according to a fifth embodiment of the disclosure, FIG. 8B is a side view of the medication concentration detecting device according to the fifth embodiment of the disclosure, and FIG. 8C is a front view of the medication concentration detecting device according to the fifth embodiment of the disclosure. In the fifth embodiment, only differences between the fifth embodiment and the first embodiment will be explained because the fifth embodiment is similar to the first embodiment. In addition, this embodiment provides a medication concentration detecting device 1*d* equipped with the light-blocking component 30' as disclosed in the fourth embodiment, but for purposes of clear explanation, the light-blocking component 30' is omitted in FIGS. 8B-8C.

Firstly, the present disclosure is not limited to the position of the first light transmitting area 30*a* and the second light transmitting area 30*b*. In this embodiment, the first light transmitting area 30*a* and the second light transmitting area 30*b* are located right above the second pipe 220 of the three-way pipe 20. In details, as shown in FIG. 8B to FIG. 8C, the first central line P1 penetrates through the light emitting component 40 disposed on the first light transmitting area 30a, and the second central line P2 penetrates through the first light receiver 50a disposed on the second light transmitting area 30b. The first central axis A1 and the second central axis A2 intersects at the point C1. Due to the position of the first light transmitting area 30a and the second light transmitting area 30b, both of the first central line P1 and the second central line P2 also can penetrate through the point C1 and form the angle 9 as discussed in the first embodiment.

Similarly, since the point C1 is located in a region at which the first pipe 210 and the second pipe 220 intersect with each other, the region has the highest concentration of the nebulized medicine M in the passageway S2 of the three-way pipe 20. Thus, the light beam L emitted by the light emitting component 40 moves toward the region having the highest concentration of the nebulized medicine M, allowing the detection of the concentration of the nebulized medicine M to be more precisely.

As the medication concentration detecting device described above, the light emitting component and the first light receiver are disposed on the three-way pipe. The light emitting component emits the light beam into the passageway, and the first light receiver receives the scattered light beam and then outputs the luminous flux signal to the processor. The processor calculates a luminous flux reference value according to the luminous flux signal from the first light receiver, and the luminous flux reference value is used for helping the patient or the health care workers to determine whether the concentration of the nebulized medicine is insufficient, thereby preventing patient from inhaling too much pure oxygen which results in oxygen toxicity. In addition, when the nebulized medicine is known to be running out, the pure oxygen provider will be turned off for preventing the waste of pure oxygen.

Moreover, in the medication concentration detecting device, the concentration of the nebulized medicine is detected in an optical manner, and thus the light beam would not interact with the medicine to affect the detection.

Furthermore, the user is able to selectively aim the light beam at the point where the first central axis of the first pipe and the second central axis of the second pipe intersect to each other. The user can also aim the light beam at the point where the first central line and the second central line intersect at the first central axis for detecting the region which has the relative high concentration of the nebulized medicine, thereby increasing accuracy of the detection.

What is claimed is:

1. A medication concentration detecting device for a nebulizer, comprising:
    a medicine container having a chamber configured for accommodating nebulized medicine;
    a three-way pipe having a passageway connected to the chamber for the nebulized medicine to flow along the passageway;
    a light emitting component disposed on the three-way pipe and configured for emitting a light beam toward the passageway;
    a first light receiver disposed on the three-way pipe and configured for receiving the light beam and outputting a luminous flux signal; and
    a processor connected to the first light receiver and configured for calculating a luminous flux reference value according to the luminous flux signal, and the luminous flux reference value being used for determining whether to output a low nebulized medicine concentration warning;
    wherein the light emitting component has a light emitting surface, the first light receiver has a light receiving surface, the light emitting surface has a first central line which is perpendicular to the light emitting surface, the light receiving surface has a second central line which is perpendicular to the light receiving surface, the three-way pipe comprises a first pipe and a second pipe, the first pipe and the second pipe surround and define the passageway, the first pipe has a first central axis, the second pipe has a second central axis, the first central axis intersects the second central axis at a point, the first central line and the second central line pass through the point.

2. The medication concentration detecting device according to claim 1, wherein the first central line and the second central line form an angle less than 180 degrees at the point.

3. The medication concentration detecting device according to claim 2, wherein the first central line and the second central line form an angle in a range from 80 degrees to 100 degrees at the point.

4. The medication concentration detecting device according to claim 1, wherein the three-way pipe is a T-shaped three-way pipe.

5. The medication concentration detecting device according to claim 1, wherein the three-way pipe further comprises a third pipe, the first pipe, the second pipe and the third pipe surround and define the passageway, the third pipe has a third central axis, the first central axis, the second central axis and the third central axis intersect at the point.

6. The medication concentration detecting device according to claim 5, wherein the first central line and the second central line form an angle less than 180 degrees at the point.

7. The medication concentration detecting device according to claim 6, wherein the first central line and the second central line form an angle in a range from 80 degrees to 100 degrees at the point.

8. The medication concentration detecting device according to claim 5, wherein the three-way pipe is a Y-shaped three-way pipe.

9. The medication concentration detecting device according to claim 1, further comprising a warning component connected to the processor, when the luminous flux reference value is lower than a predetermined lower limit value, the processor outputs a warning signal, and the warning component generates a warning information according to the warning signal.

10. The medication concentration detecting device according to claim 9, wherein the warning information comprises at least one of audio information and visual information.

11. The medication concentration detecting device according to claim 1, further comprising a light-blocking component covering a surface of the three-way pipe, the light-blocking component having a first light transmitting area and a second light transmitting area, the first light transmitting area and the second light transmitting area corresponding to the light emitting component and the first light receiver, respectively.

12. The medication concentration detecting device according to claim 11, wherein the light-blocking component and the three-way pipe are integrated into a single unit.

13. The medication concentration detecting device according to claim 11, wherein the light-blocking component is formed on the surface of the three-way pipe by a coating process.

14. The medication concentration detecting device according to claim 11, wherein the light-blocking component is detachably disposed on the surface of the three-way pipe.

15. The medication concentration detecting device according to claim 11, wherein the light-blocking component is made of at least one of paper, metal, plastic and pigment.

16. The medication concentration detecting device according to claim 11, further comprising a second light receiver disposed on the three-way pipe and located between the light emitting component and the first light receiver, the light-blocking component further having a third light transmitting area which is corresponding to the second light receiver.

17. The medication concentration detecting device according to claim 1, further comprising a second light receiver disposed on the three-way pipe and located between the light emitting component and the first light receiver.

18. The medication concentration detecting device according to claim 1, wherein the light emitting component is a light emitting diode or laser diode, the light beam has a wavelength in the range from 350 nm to 1200 nm.

19. The medication concentration detecting device according to claim 1, further comprising a notification module connected to the processor, when the luminous flux reference value is lower than a predetermined lower limit value, the notification module outputs a notification signal to a remote monitoring center.

* * * * *